(12) United States Patent
Marcel et al.

(10) Patent No.: US 7,387,778 B2
(45) Date of Patent: Jun. 17, 2008

(54) THERAPEUTIC METHODS AND COMPOSITIONS FOR THE TREATMENT OF IMPAIRED INTERPERSONAL AND BEHAVIORAL DISORDERS

(75) Inventors: Tony Marcel, Paris (FR); François Rougeon, Sevres (FR); Catherine Rougeot, Hameau de Talon (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 236 days.

(21) Appl. No.: 10/024,535

(22) Filed: Dec. 21, 2001

(65) Prior Publication Data

US 2003/0078200 A1    Apr. 24, 2003

Related U.S. Application Data

(63) Continuation-in-part of application No. PCT/EP00/06259, filed on Jun. 22, 2000.

(60) Provisional application No. 60/140,563, filed on Jun. 23, 1999.

(51) Int. Cl.
*A61K 39/00*     (2006.01)
*A61K 38/00*     (2006.01)
*C07K 5/00*      (2006.01)
*C07K 7/00*      (2006.01)

(52) U.S. Cl. .......................... 424/185.1; 514/2; 530/300; 530/330

(58) Field of Classification Search ................... 514/12; 530/300, 388.22
See application file for complete search history.

(56) References Cited

U.S. PATENT DOCUMENTS

| 6,583,147 B1 | 6/2003 | Yoo et al. |
| 2003/0078200 A1 | 4/2003 | Marcel et al. |
| 2007/0054861 A1 | 3/2007 | Rougeot et al. |

FOREIGN PATENT DOCUMENTS

| WO | WO 98/37100 | 8/1998 |

OTHER PUBLICATIONS

Pettit and Gombotz, 1998, TIBTECH, 16: 343-349.*
Rougeot, et al, 1998, Biomed. Rev., 9: 17-32.*
American Psychiatric Association: Diagnostic and Statistical Manual of Mental Disorders, Fourth Edition. Washington, DC, American Psychiatric Association, 1994, section 302.71, pp. 496-497.*
Cormio, et al, 2005, International Journal of Impotence Research, 17: 23-26.*
Newport, et al 2002, Am. J. Psychiatry, 159(8): 1265-1283.*
Rougeot, et al, 2003, Proc. Natl. Acad. Sci, 100(14): 8549-8554.*
Gee, et al, 1985, Biochem., 228: 119-126.*
Kramer, et al, 1998, Science, 281: 1640-1645.*
Takeuchi, et al, 1988, Prog. Neuro-Psychopharmacol. & Biol. Psychiat., 12: S157-S164.*
Rougeot et al., "Novel genes and hormones in salivary glands: From the gene for the submandibular rat 1 protein (SMR1) precursor to receptor sites for SMR1 mature peptides", Biomedical Reviews, vol. 9, 1998, pp. 17-32.
Rougeot C., et al., "Sialorphin, a natural inhibitor of rat membrane-bound neutral endopeptidase that displays analgesic activity.", Proc Natl Acad Sci USA. Jul. 8, 2003;100(14):8549-54. Epub Jun. 30, 2003.
Messaoudi M., et al., "The endogenous androgen-regulated sialorphin modulates male rat sexual behavior.", Horm Behav. Dec. 2004;46(5):684-91.
A. Argiolas, "Neuropeptides and sexual behaviour", Neuroscience and Biobehavioral Reviews 23 (1999) 1127-1142.
M. Messaoudi, et al., "The endogenous androgen-regulated sialorphin modulates male rat sexual behavior", Hormones and Behavior 46 (2004) 684-691.
Catherine Rougeot, et al., "Sialorphin, a natural inhibitor of rat membrane-bound neutral endopeptidase that displays analgesic activity", PNAS, Jul. 8, 2003, vol. 100, No. 14, pp. 8549-8554.
A. Benassi-Benelli, et al., "Penile Erection Induced by Apomorphine and N-n-propyl-norapomorphine in Rats", Arch. int. Pharmacodyn. 242, 241-247 (1979).
M. W. Islam, et al., "Effect of Salvia haematodes on sexual behaviour of male rats", Journal of Ethnopharmacology, 33 (1991) 67-72.
James Pfaus, et al., "What Can Animal Models Tell Us About Human Sexual Response?", pp. 1-63, 2003. Annual Review of Sex Research, 14:1-63.
"Diagnostic and Statisical Manual of Mental Disorders", The American Psychiatric Association (author), 4th Edition, 1994.
Fasano A., "Innovative strategies for the oral delivery of drugs and peptides", Trends Biotechnol., Apr. 1998; 16(4):152-7 (Abstract only).
Pontiroli AE., "Peptide hormones: Review of current and emerging uses by nasal delivery", Adv Drug Deliv Rev. Jan. 5, 1998;29(1-2):81-87 (Abstract only).
Leopold CS., "['Targeted delivery' in the gastrointestinal tract]", Med Klin (Munich). Feb. 15, 1999;94 Suppl 1:6-11 (Abstract only).
U.S. Appl. No. 10/024,535, filed Dec. 21, 2001, Marcel et al.
U.S. Appl. No. 10/620,462, filed Jul. 17, 2003, Rougeot et al.

* cited by examiner

*Primary Examiner*—Manjunath Rao
*Assistant Examiner*—Sandra Wegert
(74) *Attorney, Agent, or Firm*—Oblon, Spivak, McClelland, Maier & Neustadt, P.C.

(57) ABSTRACT

The invention relates to the field of psychopharmacology. More particularly, the invention relates to the treatment of mental disorders, such as impaired interpersonal and behavioral disorders, including sexual disorders such as M.E.D. and H.S.D.D. The invention provides new therapeutic compositions and methods for treating mental disorders, including M.E.D. and H.S.D.D. The compositions and methods according to the invention provide improved awareness and alertness to environment, improved adaptation to environment and ability to sustain attention, and increased interest in environment and capacity for arousal, without increased aggressiveness.

14 Claims, 11 Drawing Sheets

THERAPEUTIC METHODS AND COMPOSITIONS FOR THE TREATMENT OF IMPAIRED INTERPERSONAL AND BEHAVIORAL DISORDERS

This application is a continuation-in-part of PCT/EP00/06259, filed Jun. 22, 2000. Benefit under §119(e) of U.S. 60/140,563, filed Jun. 23, 1999 is also claimed.

The invention relates to the field of psychopharmacology. More particularly, the invention relates to the treatment of mental disorders, such as impaired interpersonal and behavioral disorders.

SUMMARY OF THE RELATED ART

The field of psychopharmacology has produced numerous breakthroughs in behavioral modification since the 1950s, when phenothiazines were first introduced. Unfortunately, certain types of mental disorders have proven refractory to pharmacotherapy. Among these refractory disorders are disorders which are characterized by impaired interpersonal interactions and other behavioral defects. These defects include impairment in communication, impairment of interpersonal activities, restricted reprotoire of interest, fear of partners, decreased awareness of partners similar to that seen in autism, attention deficit disorder, impairment in social functioning, solitary conduct disorders, decreased ability to relate to others, avoidance disorders, unassertive states, reactive attachment disorders, lack of social interest, impaired interpersonal functioning and relationship to the external world, impairment of self-care, decreased interest in environment, hypersomnia, and adjustment disorders with impairment in occupational functioning.

Also included in these disorders are sexual defects, including arousal disorders, impaired sexual behavior in the form of a lack of affective attention, and impaired social activity linked to sexuality. These latter disorders can manifest in part as a condition known as male erectile dysfunction (M.E.D.), a serious condition believed to affect some 8% of males worldwide. In addition, hypoactive sexual desire disorder (H.S.D.D.) is believed to affect 20% of the population worldwide, with no available therapy. Most efforts to treat M.E.D. have vasodilators to induce erection, rather than utilizing behavior modifiers. For example, PDE5 inhibitors, such as sildenafil, alpha blocking agents, such as moxysylate or phentolamine, and prostaglandins have been used. Unfortunately, these treatments suffer from certain deficiencies. The PDE5 inhibitors, for example, are subject to degradation via the cytochrome P450 degradation pathway. Prostaglandins require unpleasant intracavernous or intra-urethral administration. In addition, none of these treatments directly affects the emotional, affectionate aspects of the sexual relationship.

All above disorders are actually listed in the DSM-IV-TR™ classification, as described in Diagnostic and Statistical Manual of Mental Disorders, American Psychiatric Assoc., fourth edition, 2000.

There is, therefore, a need for new therapeutic compositions and methods for treating mental disorders, including M.E.D. and H.S.D.D. Ideally, such compositions and methods should provide improved awareness and alertness to environment, improved adaptation to environment and ability to sustain attention, and increased interest in environment and capacity for arousal, without increased aggressiveness.

Many central peptides, known as neuropeptides, have effects on behavior. For example, Mondal et al., B.B.R.C. 256: 495-499 (1999) teaches that the neuropeptide orexin can be used to treat eating disorders. Insel et al., Reviews of Reproduction 2: 28-37 (1997) discloses that oxytocin, a neurohypophyseal peptide can influence reproductive behavior. Unfortunately, oxytocin can produce unwanted side effects in male subjects. For example, Uvnaes-Moberg et al., Pharmacology, Biochemistry and Behavior 49: 101-106 (1994) teaches that high doses of oxytocin decrease locomotion and low doses of oxytocin cause an anxiolytic-like effect in male rats. Thus, neuropeptides have shown limitations as therapeutics for mental disorders, particularly for sexual disorders.

Rosinski-Chupin et al. U.S. Pat. No. 5,859,189 (1999) discloses a purified pentapeptide or tetrapeptide expressed in the submaxillary gland of the rat, and suggests that it may fulfil an important function specific for the male. However, Rougeot et al., Amer. J. Physiol. 273: R1309—R1320 (1997) discloses biodistribution for this peptide with autoradiographs that suggest that the peptide does not cross the blood brain barrier. Thus, this peptide would not be expected to be a promising candidate for behavior modification, especially direct neuro or psycho behavioral modifications.

The identification of Neutral EndoPeptidase 24-11 (NEP), also named Enkephalinase, as a cellular receptor for SMR1-peptide comes as a confirmation (application EP00403670.3).

BRIEF SUMMARY OF THE INVENTION

The invention provides new therapeutic compositions and methods for treating mental disorders, including M.E.D. The compositions and methods according to the invention provide improved awareness and alertness to environment, improved adaptation to environment and ability to sustain attention, and increased interest in environment and capacity for arousal, without increased aggressiveness.

The present inventor has surprisingly discovered that peptides of the type disclosed in U.S. Pat. No. 5,859,189 are effective as therapeutics for mental disorders, including without limitation sexual disorders.

In a first aspect, the invention provides methods for treating mental disorders. The methods according to the invention comprise administering to a mammal having a mental disorder an amount of a peptide or a peptidomimetic according to the invention that is sufficient to reduce or eliminate symptoms of the mental disorder.

In certain preferred embodiments, the mental disorder is impaired interpersonal interactions or other behavioral defects including those resulting from autistic disorders or schizophrenia. In certain preferred embodiments, the mental disorder is an avoidance disorder. In certain preferred embodiments, the mental disorder is a decreased awareness disorder. In certain preferred embodiments, the mental disorder is an attention deficit disorder. In certain preferred embodiments, the mental disorder is an arousal disorder. In certain preferred embodiments, the mental disorder is impaired interpersonal functioning and relationship to the external world. In certain preferred embodiments, the mental disorder is impaired social activity linked to sexuality. In certain preferred embodiments, the mental disorder is impaired sexual behavior. In certain preferred embodiments, the mental disorder is a mood disorder. In certain preferred embodiments, the mental disorder is a depressive disorder. In certain preferred embodiments, the mental disorder is simple phobia, social phobia, obsessive-compulsive disorder, or acute stress disorder. In certain preferred embodiments, the mental disorder is related to a pain disorder. In certain preferred embodiments, the mental disorder comprises symptoms of more than one of these disorders.

In certain preferred embodiments, the peptide or peptidomimetic according to the invention is administered together with a second pharmaceutical, wherein the second pharmaceutical agent is present in an amount insufficient to reduce or eliminate symptoms of the mental disorder, and wherein the peptide or peptidomimetic according to the invention and the second pharmaceutical agent act synergistically to reduce or eliminate symptoms of the mental disorder.

In a second aspect, the invention provides therapeutic compositions comprising a peptide or peptidomimetic according to the invention in an amount sufficient to reduce or eliminate symptoms of a mental disorder in a mammal having the mental disorder, and further comprising a pharmaceutically acceptable diluent and/or buffer and/or excipient.

In certain preferred embodiments, the therapeutic composition is useful in preparing a medicament for the treatment of impaired interpersonal interactions or other behavioral defects including those resulting from autistic disorders or schizophrenia. In certain preferred embodiments, the therapeutic composition is useful in preparing a medicament for the treatment of an avoidance disorder. In certain preferred embodiments, the therapeutic composition is useful in preparing a medicament for the treatment of a decreased awareness disorder. In certain preferred embodiments, the therapeutic composition is useful in preparing a medicament for the treatment of an attention deficit disorder. In certain preferred embodiments, the therapeutic composition is useful in preparing a medicament for the treatment of an arousal disorder. In certain preferred embodiments, the therapeutic composition is useful in preparing a medicament for the treatment of impaired interpersonal functioning and relationship to the external world. In certain preferred embodiments, the therapeutic composition is useful in preparing a medicament for the treatment of impaired social activity linked to sexuality. In certain preferred embodiments, the therapeutic composition is useful in preparing a medicament for the treatment of impaired sexual behavior. In certain preferred embodiments, the therapeutic composition is useful in preparing a medicament for the treatment of a mood disorder. In certain preferred embodiments, the therapeutic composition is useful in preparing a medicament for the treatment of a depressive disorder. In certain preferred embodiments, the therapeutic composition is useful in preparing a medicament for the treatment of simple phobia, social phobia, obsessive-compulsive disorder, or acute stress disorder. In certain preferred embodiments, the therapeutic composition is useful in preparing a medicament for the treatment of a mental disorder related to a pain disorder. In certain preferred embodiments, the therapeutic composition is useful in preparing a medicament for the treatment of symptoms of more than one of these disorders.

In certain preferred embodiments, the peptide or peptidomimetic according to the invention is present in the therapeutic composition according to the invention together with a second pharmaceutical, wherein the second pharmaceutical agent is present in an amount insufficient to reduce or eliminate symptoms of the mental disorder, and wherein the peptide or peptidomimetic according to the invention and the second pharmaceutical agent act synergistically to reduce or eliminate symptoms of the mental disorder.

DETAILED DESCRIPTION OF THE PREFERRED EMBODIMENTS

Figure 1:
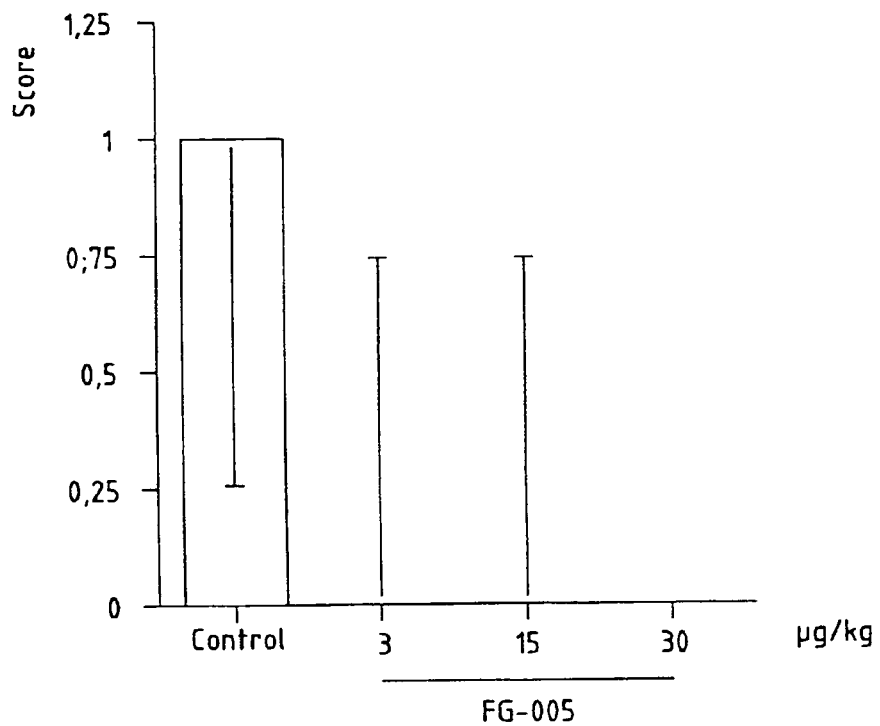
FIG. 1 shows sleep results in an Irwin test on rats administered escalating doses of a preferred embodiment of a peptide according to the invention.

The invention relates to the field of psychopharmacology. More particularly, the invention relates to the treatment of mental disorders, such as impaired interpersonal and behavioral disorders, including sexual disorders such as M.E.D.

The patents and publications cited in this specification evidence the knowledge in this field and are hereby incorporated by reference in entirety. In the case of conflict between any teaching of a reference cited in this specification and any teaching specifically disclosed in this specification, the teaching specifically disclosed in this specification shall prevail.

The invention provides new therapeutic compositions and methods for treating mental disorders, including M.E.D. The compositions and methods according to the invention provide improved awareness and alertness to environment, improved adaptation to environment and ability to sustain attention, and increased interest in environment and capacity for arousal, without increased aggressiveness. The present inventor has surprisingly discovered that peptides of the type disclosed in U.S. Pat. No. 5,859,189 are effective as therapeutics for mental disorders, including without limitation sexual disorders.

In a first aspect, the invention provides methods for treating mental disorders. The methods according to the invention comprise administering to a mammal having a mental disorder an amount of a SMR1-peptide or a peptidomimetic that is sufficient to reduce or eliminate symptoms of the mental disorder.

For purposes of the invention, the term "mammal" is used in its usual taxonomic sense and specifically includes humans.

For purposes of the invention, a "peptide" is a molecule comprised of a linear array of amino acid residues connected to each other in the linear array by peptide bonds. Such linear array may optionally be cyclic, i.e., the ends of the linear peptide or the side chains of amino acids within the peptide may be joined, e.g., by a chemical bond. Such peptides according to the invention may include from about three to about 500 amino acids, and may further include secondary, tertiary or quaternary structures, as well as intermolecular associations with other peptides or other non-peptide molecules. Such intermolecular associations may be through, without limitation, covalent bonding (e.g., through disulfide linkages), or through chelation, electrostatic interactions, hydrophobic interactions, hydrogen bonding, ion-dipole interactions, dipole-dipole interactions, or any combination of the above.

As used in the present specification, SMR1-peptide means the SMR1 protein, a peptide generated from SMR1, also called a maturation product of the SMR1 protein, or one of the biologically active derivatives of said protein or said maturation product.

In a preferred embodiment, the SMR1-peptide is a compound of structural formula (1): $X_1QHX_2X_3X_4$ wherein $X_1$ denotes a hydrogen atom or $X_1$ represents an amino acid chain selected from the following: $X_1$=R or G, $X_1$=RR, or $X_1$=PRR, or $X_1$=GPRR, or $X_1$=RGPRR, or $X_1$=VRGPRR, $X_2$ denotes N, G or D, $X_3$ denotes P or L, and $X_4$ denotes R or T.

Preferred peptides according to the invention comprise an amino acid sequence selected from the group consisting of:

```
Glp-His-Asn-Pro-Arg          [SEQ ID NO. 1]

Gln-His-Asn-Pro-Arg (QHNPR)  [SEQ ID NO. 2]

RQHNPR                       [SEQ ID NO. 5]

VRGPRRQHNPR                  [SEQ ID NO. 6]

QHNLR                        [SEQ ID NO. 7]

RQHNLR                       [SEQ ID NO. 8]
```

-continued
```
GQHGPR                       [SEQ ID NO. 9]

GQHDPT                       [SEQ ID NO. 10]
``` wherein the sequences are shown in N to C configuration.

Still preferably, the SMR1-peptide according to the invention is selected form the group consisting of:

```
Glp-His-Asn-Pro              [SEQ ID NO. 3], and

Gln-His-Asn-Pro (QHNP)       [SEQ ID NO. 4].
```

In the herein disclosed aminoacid sequences:
Q or Gln represent Glutamine,
H or H is represent Histidine,
N or Asn represent Asparagine,
Glp represents pyroglutamate,
G or Gly represent Glycine,
P or Pro represent Proline,
R or Arg represent Arginine,
L or Leu represent Leucine,
T or Thr represent Threonine,
V or Val represent Valine, and
D or Asp represent Aspartic acid.

Certain particularly preferred peptides according to the invention consist essentially of an amino acid sequence selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, and SEQ ID NO. 10.

Certain most preferred peptides according to the invention consist of an amino acid sequence selected from the group consisting of SEQ ID NO. 1, SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, and SEQ ID NO. 10.

In these peptides, by N-terminal cyclization/decyclization, Glp and Gln interconvert.

"Biologically active derivatives" of the SMR1 protein refer to function-conservative variants, homologous, and peptidomimetic proteins that preferably retain the binding specificity and/or physiological activity of the parent peptide, as defined below. For instance, biologically active derivatives of SMR1 can be identified by a process for screening ligand molecules that specifically bind to the target receptor for the QHNPR pentapeptide, according to the method described in WO 98/37100, incorporated by reference herein.

"Function-conservative variants" are those in which a given amino acid residue in a protein has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, and lysine are hydrophilic-basic amino acids and may be interchangeable. Similarly, isoleucine, a hydrophobic amino acid, may be replaced with leucine, or valine. Such changes are expected to have little or no effect on the apparent molecular weight or isoelectric point of the protein or polypeptide. Amino acids other than those indicated as conserved may differ in a protein or enzyme so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide or enzyme which has at least 60% amino acid identity as determined by BLAST or FASTA algorithms, preferably at least 75%, most preferably at least 85%, and even more preferably at least 90%, and which has the same or substantially similar properties or functions as the native or parent protein or enzyme to which it is compared.

"Allelic variants" are more particularly encompassed, as described in greater details below.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins have sequence homology, as reflected by their sequence similarity, whether in terms of percent similarity or the presence of specific residues or motifs at conserved positions.

Accordingly, the term "sequence similarity" in all its grammatical forms refers to the degree of identity or correspondence between amino acid sequences of proteins that may or may not share a common evolutionary origin (see Reeck et al., supra). However, in common usage and in the instant application, the term "homologous," when modified with an adverb such as "highly," may refer to sequence similarity and may or may not relate to a common evolutionary origin.

In a particular embodiment, two amino acid sequences are "substantially homologous" or "substantially similar" when greater than 80% of the amino acids are identical, or greater than about 90% are similar and functionally identical. Preferably, the similar or homologous sequences are identified by alignment using, for example, the GCG (Genetics Computer Group, Program Manual for the GCG Package, Version 7, Madison, Wis.) pileup program, or any of the programs described above (BLAST, FASTA, etc.).

In addition, certain preferred peptides according to the invention comprise, consist essentially of, or consist of an allelic variant of a peptide shown in any of SEQ ID NOS. I-10. As used herein, an "allelic variant" is a peptide having from one to two amino acid substitutions from a parent peptide, but retaining the binding specificity and/or physiological activity of the parent peptide. As used herein, "retaining the binding specificity of the parent peptide" means being able to bind to a monoclonal antibody that binds to one of the peptides shown in SEQ ID NOS. 1-10 with an affinity that is at least one-tenth, more preferably at least one-half, and most preferably at least as great as that of one of the actual peptides shown in SEQ ID NOS. 1-10. Determination of such affinity is preferably conducted under standard competitive binding immunoassay conditions (Rougeot et al., Eur J Biochem 1994 219(3):765-73). "Retaining the physiological activity of the parent peptide" means retaining the ability of any one of the peptides shown in SEQ ID NOS. 1-10 to reduce or eliminate symptoms of a mental disorder. Determining whether such symptoms are reduced or eliminated is further described later in this specification. The term "allelic variants" is specifically intended to include any human functional homolog of the peptides set forth in SEQ ID NOS. 1-10 that do not have the identical amino acid sequence thereof.

Peptides according to the invention can be conveniently synthesized using art recognized techniques (see e.g., Merrifield, J. Am. Chem. Soc. 85: 2149-2154).

Preferred peptidomimetics retain the binding specificity and/or physiological activity of the parent peptide, as described above. As used herein, a "peptidomimetic" is an organic molecule that mimics some properties of peptides, preferably their binding specificity and physiological activity. Preferred peptidomimetics are obtained by structural modification of peptides according to the invention, preferably using unnatural amino acids, conformational restraints, isosteric replacement, cyclization or other modifications. Other preferred modifications include without limitation, those in which one or more amide bond is replaced by a non-amide bond, and/or one or more amino acid side chain is replaced by a different chemical moiety, or any one or more of the N-terminus, the C-terminus or one or more side chain is protected by a protecting group, and/or double bonds and/or cyclization and/or stereospecificity is introduced into the amino acid chain to increase rigidity and/or binding affinity.

Still other preferred modifications include those intented to enhance resistance to enzymatic degradation, improvement in the bioavailability in particular by nervous, and gonad tissues and more generally in the pharmacokinetic properties and especially comprise:

protecting the NH2 and COOH hydrophilic groups by esterification (COOH) with lipophilic alcohols or by amidation (COOH) and/or by acetylation (NH2) or added carboxyalkyl or aromatic hydrophobic chain at the NH2 terminus;

retroinversion or reduction isomers of the CO—NH amide bonds or methylation (or ketomethylene, methyleneoxy, hydroxyethylene) of the amide functions;

substitution of L aminoacids for D aminoacids.

dimerization of amino acid peptide chain.

All of these variations are well known in the art. Thus, given the peptide sequences disclosed herein, those skilled in the art are enabled to design and produce peptidomimetics having binding characteristics similar to or superior to such peptides (see e.g., Horwell et al., Bioorg. Med. Chem. 4: 1573 (1996); Liskamp et al., Recl. Trav. Chim. Pays-Bas 1: 113 (1994); Gante et al., Angew. Chem. Int. Ed. Engl. 33: 1699 (1994); Seebach et al., Helv. Chim. Acta 79: 913 (1996)).

As used herein, "having a mental disorder" means manifesting at least one clinically observable behavior or physical characteristic that is generally recognized as a symptom of a mental disorder. The term "to reduce or eliminate symptoms of a mental disorder" means to obtain a clinically observable beneficial change in one or more behavior or physical characteristic that is generally recognized as a symptom of a mental disorder. Mental disorders are diagnostic categories for which criteria are provided by a manual written by working groups of psychiatrists. This manual is published by the American Psychiatric Association, "Diagnostic and Statistical Manual of Mental Disorders", 1992, which is hereby incorporated by reference. Each of the disorders discussed below are well known, as evidenced by their treatment in this manual. Thus, only brief definitions are provided herein for the disorders discussed below.

In certain preferred embodiments, the mental disorder is an avoidance disorder. As used herein, an "avoidance disorder" means a disorder having as an essential feature a pervasive pattern of social discomfort, fear of negative evaluation, and timidity. It includes excessive shrinking from contact with unfamiliar people. The present invention particularly relates to avoidant disorder personalities defined as pervasive pattern of social inhibition", feeling of inadequacy, and hypersensitivity to negative evaluation, beginning by early adulthood and present in a variety of contexts (DSM-IV-TR coded 301.82, p 718-21 of Diagnostic and Statistical Manual of Mental Disorders, American Psychiatric Assoc., 1992).

In certain preferred embodiments, the mental disorder is a decreased awareness disorder. As used herein, a "decreased awareness disorder" means a disorder marked by lack of awareness of the existence or feelings of others (e.g. treats a person like if he or she were a piece of furniture; does not notice another person's distress). These disorders can results from an autistic disorder.

In certain preferred embodiments, the mental disorder is an attention deficit/hyperactivity disorder. As used herein, an "attention deficit disorder" means a disturbance in which the predominant feature is the persistence of developmentally inappropriate and marked inattention. Deficit/hyperactivity disorders also include combined type, predominantly inattentive type, and hyperactive-impulsive type (DSM-IV-TR coded 314.01, 314,00, 314,01, p 87-93 of Diagnostic and Statistical Manual of Mental Disorders, American Psychiatric Assoc., 1992).

In certain preferred embodiments, the mental disorder is an arousal disorder. As used herein, an "arousal disorder" means a reactive attachment disorder such as persistent failure to initiate or respond to most social interactions. This can lead to severe forms in children that have been called "failure to thrive" or "hospitalism". Decreased interest in environment is another element of reactive attachment disorders, commonly manifested as insufficient visual tracking of eyes, faces or voices, absence of reaching out to objects.

In certain preferred embodiments, the mental disorder is impaired interpersonal functioning and relationship to the external world. As used herein, "impaired interpersonal functioning and relationship to the external world" means other interpersonal problems, examples of which are difficulties with co-workers or with romantic partners. These disorders include schizoid personality disorder, which is a pervasive pattern of indifference to social relationships and a restricted range of emotional experience and expression, and also include schizophrenia or depressive disorder.

In certain preferred embodiments, the mental disorder is a mood disorder, with special reference to dysthymic disorder (mental coded 300.4, p 380-1 in Diagnostic and Statistical Manual of Mental Disorders, American Psychiatric Assoc., 1992), and depressive disorder no otherwise specified (mental, p 381-2 in Diagnostic and Statistical Manual of Mental Disorders, American Psychiatric Assoc., 1992); cyclothymic disorder and bipolar disorder not otherwise specified (mental coded 301-13 and 296.80, respectively, p 400 in Diagnostic and Statistical Manual of Mental Disorders, American Psychiatric Assoc., 1992).

In certain preferred embodiments, the mental disorder is impaired social activity linked to sexuality. As used herein, "impaired social activity linked to sexuality" is impairment of social relationship to a sexual partner, which can lead to impairment of occupational functioning.

In certain preferred embodiments, the mental disorder is impaired sexual behavior. As used herein, "impaired sexual behavior" includes sexual and gender identity disorders with special reference to hypoactive sexual desire disorder (H.S.D.D., mental coded 302.71, p 543-4 in Diagnostic and Statistical Manual of Mental Disorders, American Psychiatric Assoc., 1992), defined as persistently or recurrently deficient or absent sexual fantasies and desire for sexual activity, and further includes feelings of inadequacy concerning sexual performance such as untimely ejaculation.

In certain preferred embodiments, the mental disorder is simple phobia (mental coded 300.29, p 443-9), social phobia (mental coded 300.23, p 450), obsessive-compulsive disorder (mental coded 300.3, p 456-63), or acute stress disorder (mental coded 308.3, p 471-2), according to the references of Diagnostic and Statistical Manual of Mental Disorders, American Psychiatric Assoc., 1992.

In certain preferred embodiments, the mental disorder is further related to pain disorders, either associated with psychological factors, or with both psychological factors and a general medical condition or with a general condition (mental coded 307.80, p 499-503 in Diagnostic and Statistical Manual of Mental Disorders, American Psychiatric Assoc., 1992).

In certain preferred embodiments, the mental disorder comprises symptoms of more than one of these disorders.

In the methods according to the invention, the peptides or peptidomimetics according to the invention may be administered by any of a variety of means. In certain preferred embodiments, administration may be parenteral, most preferably intravenous. In other preferred embodiments, administration may be intranasal, oral, sublingual, transmucosal, intrarespiratory, or through an inert or iontophoretic patch.

Dosages of the peptide or peptidomimetic to be administered will depend on the particular patient, the condition, and the route of administration, and can be determined empirically by observing the reduction or elimination of symptoms of a mental disorder in response to an elevating dosage regimen. Preferred dosages are from about 0.1 µg/kg to about 1 mg/kg, more preferably from about 1 µg/kg to about 100 µg/kg, and most preferably from about 1 µg/kg to about 50 µg/kg.

In certain preferred embodiments, the peptide or peptidomimetic according to the invention is administered together with a second pharmaceutical agent, wherein the second pharmaceutical agent is present in an amount insufficient to reduce or eliminate symptoms of the mental disorder, and wherein the peptide or peptidomimetic according to the invention and the second pharmaceutical agent act synergistically to reduce or eliminate symptoms of the mental disorder. Administration of the peptide or peptidomimetic according to the invention and the second pharmaceutical agent can be simultaneous, sequential, or alternating. As used herein, a "pharmaceutical agent" is a substance other than food, water or air that mediates a beneficial physiological response at a sublethal concentration when administered to a mammal. Preferred second pharmaceutical agents include those currently used to treat mental disorders, including M.E.D. "Synergistically" means that the peptide or the peptidomimetic and the second pharmaceutical agent together are more effective in reducing or eliminating symptoms of a mental disorder than either one alone would be at the same concentration.

The methods according to the invention are useful for animal model studies of mental disorders. The methods of the invention are also useful in treating mammals, including humans, for sexual disorders and other mental disorders.

In a second aspect, the invention provides therapeutic compositions comprising a peptide or peptidomimetic according to the invention in an amount sufficient to reduce or eliminate symptoms of a mental disorder in a mammal having the mental disorder, and further comprising a pharmaceutically acceptable diluent and/or buffer and/or excipient.

According to this aspect of the invention, the terms "peptide", "peptidomimetic", and "to reduce or eliminate symptoms of the mental disorder" are used as described for the first aspect of the invention. The terms "pharmaceutically acceptable", "diluent", "buffer" and "excipient" are used in their usual sense within the industry. The therapeutic composition may preferably be in the form of a solid, a liquid, a gel, an aerosol, or a sustained release formulation.

In certain preferred embodiments, the mental disorder is impaired interpersonal interactions or other behavioral defects including those resulting from autistic disorders or schizophrenia. In certain preferred embodiments, the therapeutic composition is useful in preparing a medicament for the treatment of an avoidance disorder. In certain preferred embodiments, the therapeutic composition is useful in preparing a medicament for the treatment of a decreased awareness disorder. In certain preferred embodiments, the therapeutic composition is useful in preparing a medicament for the treatment of an attention deficit disorder. In certain preferred embodiments, the therapeutic composition is useful in preparing a medicament for the treatment of an arousal disorder. In certain preferred embodiments, the therapeutic composition is useful in preparing a medicament for the treatment of impaired interpersonal functioning and relationship to the external world. In certain preferred embodiments, the therapeutic composition is useful in preparing a medicament for the treatment of impaired social activity linked to sexuality. In certain preferred embodiments, the therapeutic composition is useful in preparing a medicament for the treatment of impaired sexual behavior. Each of these disorders are as defined for the first aspect of the invention. In certain preferred embodiments, the therapeutic composition is useful in preparing a medicament for the treatment of a mood disorder. In certain preferred embodiments, the therapeutic composition is useful in preparing a medicament for the treatment of a depressive disorder. In certain preferred embodiments, the therapeutic composition is useful in preparing a medicament for the treatment of simple phobia, social phobia, obsessive-compulsive disorder, or acute stress disorder. In certain preferred embodiments, the therapeutic composition is useful in preparing a medicament for the treatment of a mental disorder relating to a pain disorder. In certain preferred embodiments, the therapeutic composition is useful in preparing a medicament for the treatment of symptoms of more than one of these disorders.

In certain preferred embodiments, the peptide or peptidomimetic according to the invention is present in the therapeutic composition according to the invention together with a second pharmaceutical agent, wherein the second pharmaceutical agent is present in an amount insufficient to reduce or eliminate symptoms of the mental disorder, and wherein the peptide or peptidomimetic according to the invention and the second pharmaceutical agent act synergistically to reduce or eliminate symptoms of the mental disorder.

The therapeutic compositions according to the invention are useful for the preparation of medicaments, and are useful in the methods according to the invention.

The following examples are provided to further illustrate certain preferred embodiments of the invention and are not intended in any way to limit the scope of the invention.

EXAMPLE 1

Synthesis of FG-005

The FG-005 peptide (SMR1-QHNPR) was synthesized, for FGene by Bachem AG. The pentapeptide has a Glutamine at its N-terminal end which tends to transform (cyclization) into a pyroglutamate when in an aqueous phase but the peptide retains its biological properties. The synthesized peptide had a purity of more than 91% of its non-cyclic structure and 5% of its cyclic structure. It was conditioned under a neutral gas atmosphere (Argon) in vials of 500 µg to be opened just prior to each experiment. Purity and structure were checked by HPLC and Mass Spectroscopy. Prior to injection, FG-005 was resuspended in a solution of Acetic acid 0.01N and PBS. Three concentrations were tested 0, 3, 15 and 30 µg/kg.

In the following examples, non-treated rats means rats injected with vehicle as control.

EXAMPLE 2

Irwin Test

An Irwin test was performed on 12 male Wistar rats (Iffa Credo, L'Arbresles, France), weighing 260-280 g. They were housed in groups of 4 in a climate controlled room with a 12 h light:dark cycle (light 8:00 PM-8:00 AM) and had access to food and water ad libitum. After a seven day acclimatization period, the rats were weighed, identified and randomly assigned to one of the four treatment groups. The drug was injected to the tail vein of the rats according to the group dose.

Figure 2:
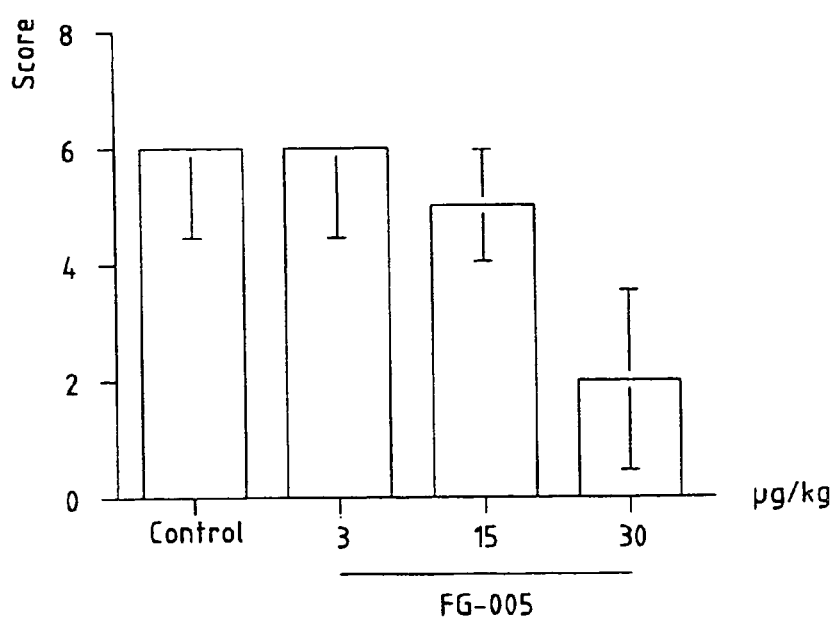
FIG. 2 shows results of a startle response test on rats administered escalating doses of a preferred embodiment of a peptide according to the invention.
Figure 3:
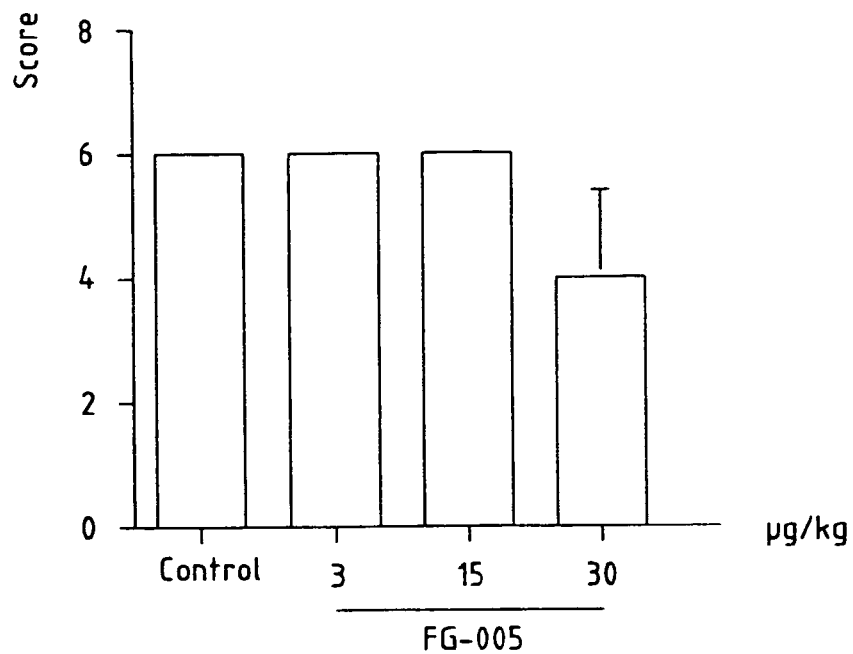
FIG. 3 shows results of an abdominal tone test on rats administered escalating doses of a preferred embodiment of a peptide according to the invention.
Figure 4:
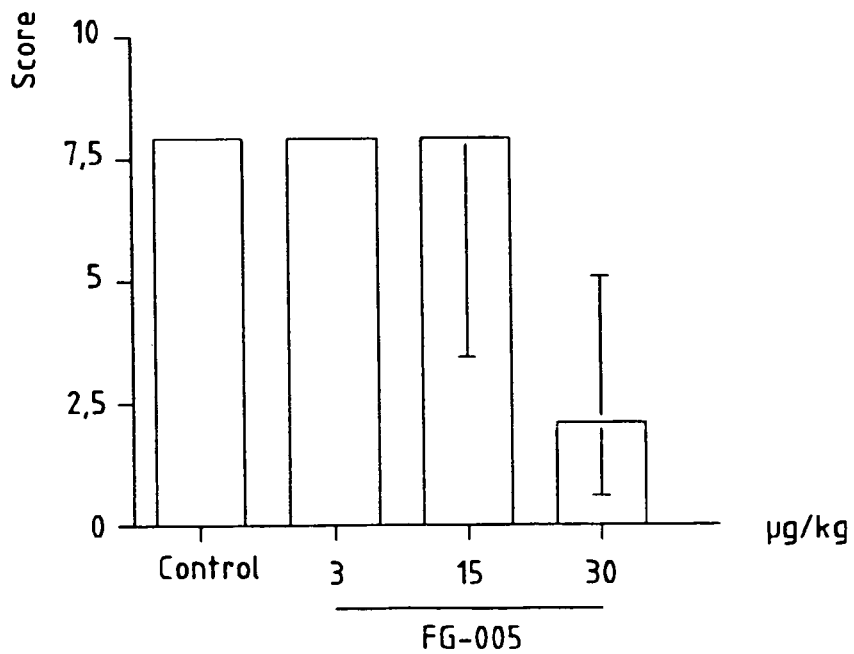
FIG. 4 shows results of a tail pinch test at 15 minutes on rats administered escalating doses of a preferred embodiment of a peptide according to the invention.
Figure 5:
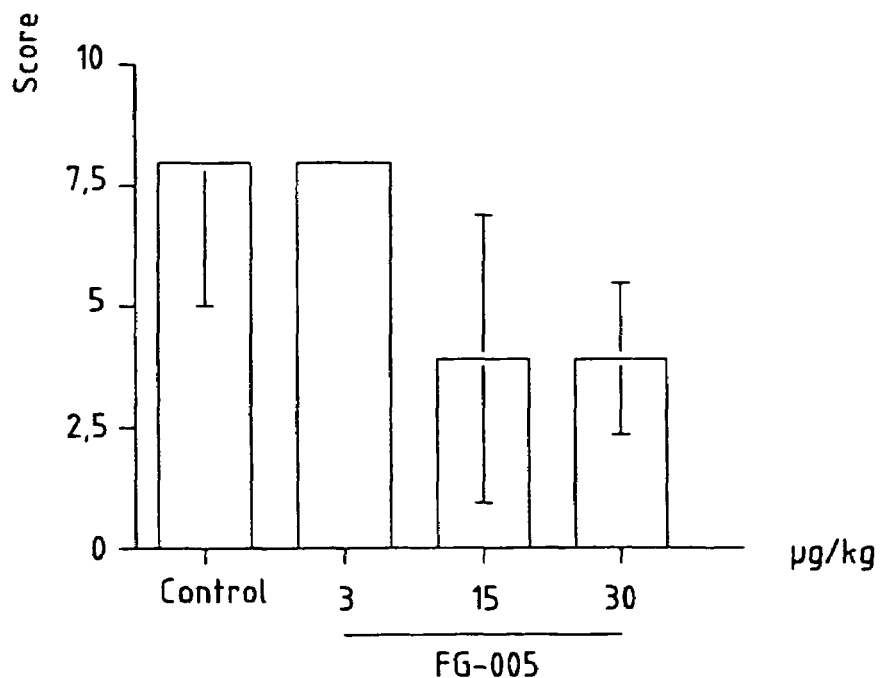
FIG. 5 shows results of a tail pinch test at 30 minutes on rats administered escalating doses of a preferred embodiment of a peptide according to the invention.
Figure 6:
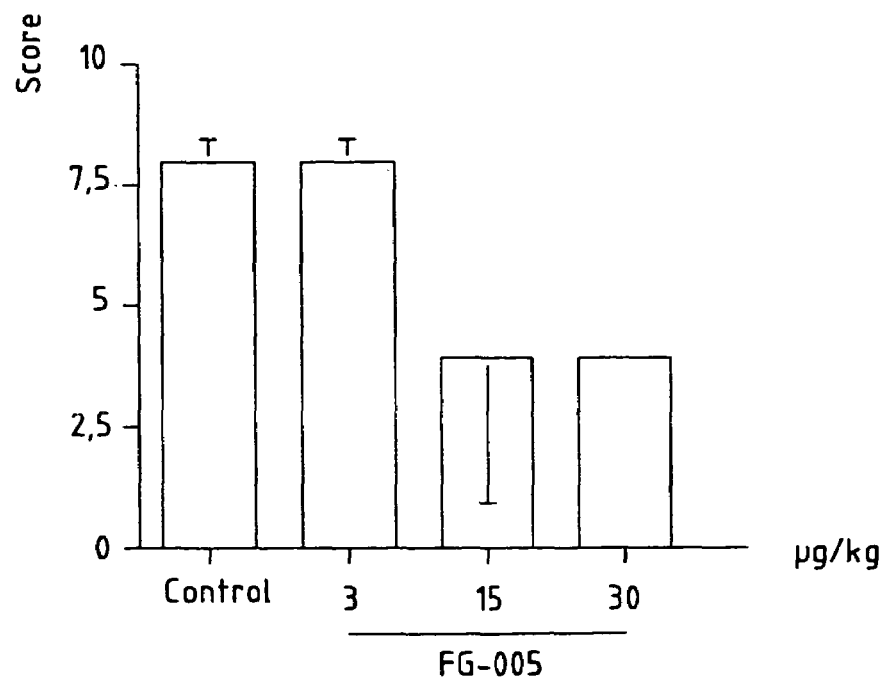
FIG. 6 shows results of a tail pinch test at 60 minutes on rats administered escalating doses of a preferred embodiment of a peptide according to the invention.
Figure 7:
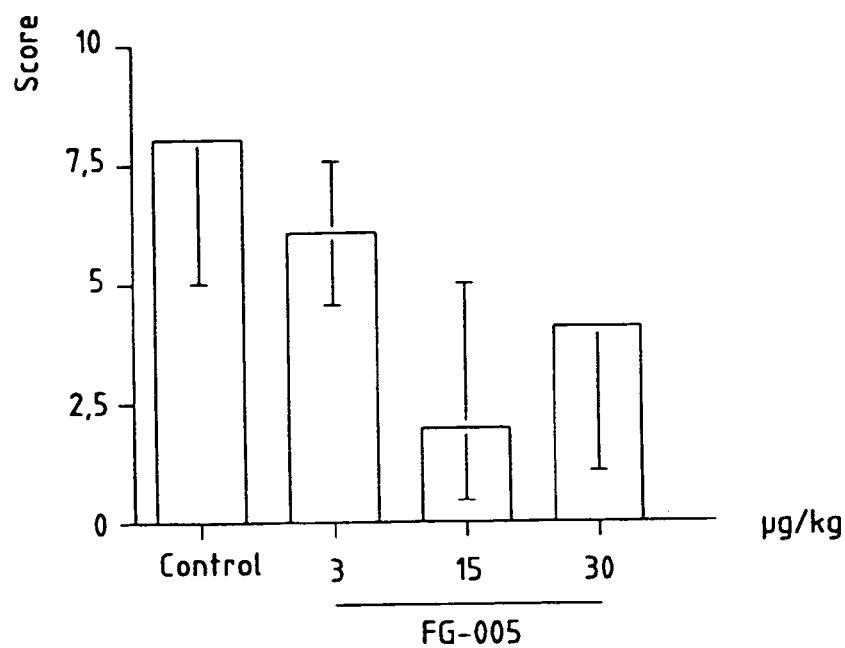
FIG. 7 shows results of a tail pinch test at 120 minutes on rats administered escalating doses of a preferred embodiment of a peptide according to the invention.

Observations were performed 15, 30, 60 and 120 minutes after administration. Among the most noticeable results are the results concerning the awareness state of the rats. As shown in FIG. 1, rats are much more aware and alert to the environment and are much less likely to fall asleep after 2 hours of tests when injected with FG-005 peptide (SMR1-QHNPR). Significant response to the wire maneuver test demonstrates improved adaptation to environment and ability to sustain attention. Their increased interest in environment and capacity for arousal is demonstrated by increased interest in the finger approach test, and increased vocalization when third parties approach. This increased alertness and vigilance is not associated with an increase of aggressiveness. Rats injected FG-005 are less stressed as shown by startle response test (FIG. 2), and by the abdominal tone (FIG. 3). They demonstrate less reactivity to nociceptive stimuli as shown by the tail pinch test (FIGS. 4, 5, 6, 7).

EXAMPLE 3

Behavior of Male Rats in the Presence of Females

Behavior tests were performed on 12 male Wistar rats (Iffa Credo, L'Arbresles, France), weighing 260-280 g. They were housed in groups of 4 in a climate controlled room with a 12-h light:dark cycle and had access to food and water ad libitum. After seven days acclimatization period, the rats were weighed, identified and randomly assigned to one of the four treatment groups. The rats were familiarized once with female rats which had been brought to sexual receptivity by injecting estradiol benzoate for 4 days (5 µg/0.5 ml oil, s.c. once daily). Behavioral testing was performed under blind conditions in a dimlight environment 2 hours after the onset of the dark phase of the light/dark cycle. Behavior was assessed by placing the male rat in a plexiglass cage (50×30×20 cm) five minutes before a receptive female was presented. All of the tests on rats were recorded on a VHS-videotape. The recorded parameters were: number of ejaculations, latency of first mount, latency of first ejaculation, number of mounts, postejaculatory interval, avoidance behavior patterns, awareness of other rats presence, initiation or response to social interaction, interest in other rat, self-care, willingness to enter into relationship. All of the quantitative results were analyzed using the Kruskal-Wallis test followed by the Mann-Whitney U-Test to compare each treated group with the control group. The statistical analyzes were carried out using the Statview 4.1 statistical package.

EXAMPLE 4

Latency of the First Mount

Figure 8:
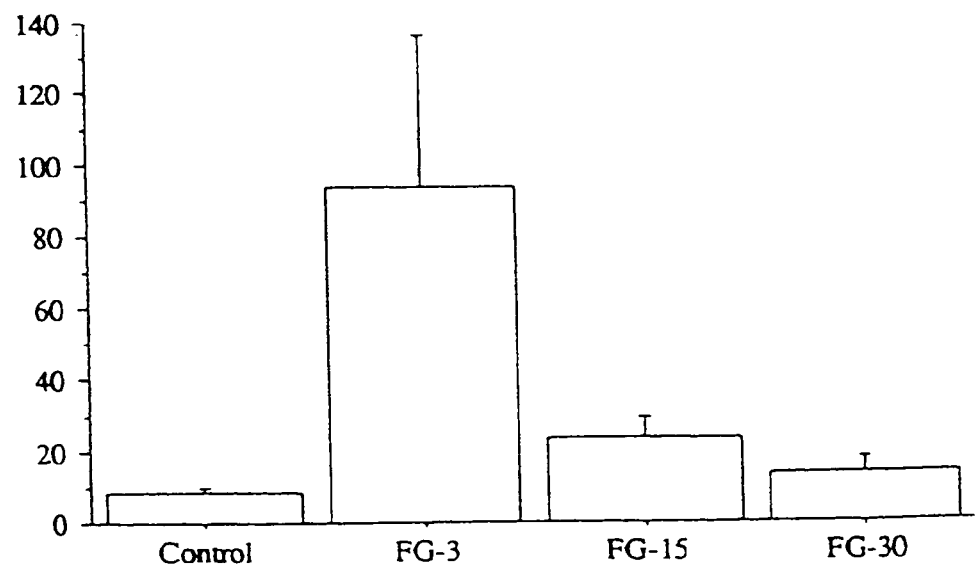
FIG. 8 shows results of a latency of the first mount test on rats administered escalating doses of a preferred embodiment of a peptide according to the invention.

The VHS-video recorded study of the behavior of the rats showed that rats at a dose of FG-005 peptide (SMR1-QH-NPR) 3 µg/kg exhibited a significantly increased latency of first mounts (see Table I and FIG. 8). Treated rats are more aware of their partner's presence and considerably increase their signs of interest in the other rat. Social interaction and interpersonal activities before sexual intercourse are significantly increased.

TABLE I

|  | Number | Mean (sec.) | Std. Deviation | Std. Error | r |
|---|---|---|---|---|---|
| Control | 3 | 8.333 | 2.887 | 1.667 |  |
| 3 µg/kg | 3 | 93.333 | 73.711 | 42.557 | 0.0238 |
| 15 µg/kg | 3 | 23.000 | 10.440 | 6.028 | 0.6439 |
| 30 µg/kg | 3 | 13.667 | 6.658 | 3.844 | 0.8657 |

EXAMPLE 5

Ejaculations, Self-Care and Interest in Other Rat

Figure 9:
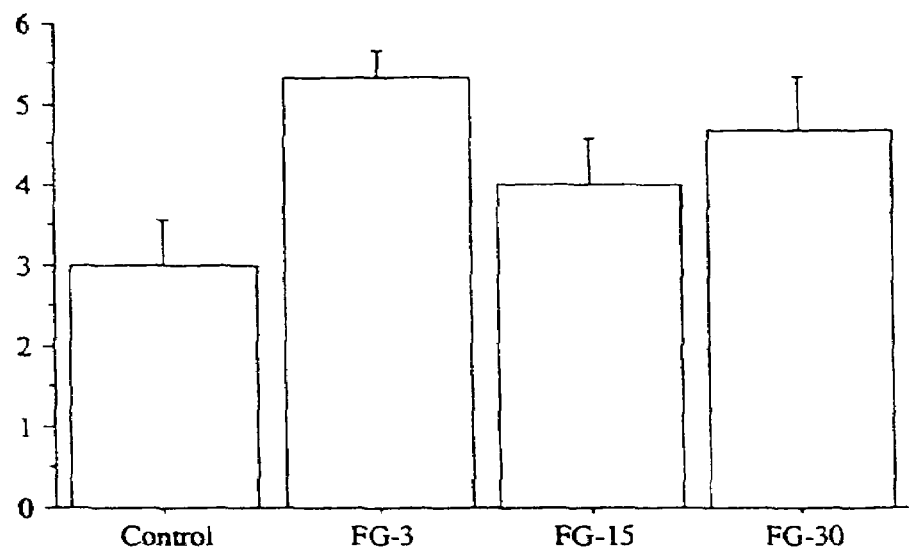
FIG. 9 shows results of a number of ejaculations test on rats administered escalating doses of a preferred embodiment of a peptide according to the invention.

The number of episodes of intercourse (as measured by number of ejaculations in 45 minutes) are significantly increased (see Table II and FIG. 9). After each penetration, rat's self-care, and attention to personal toilet is increased. After ejaculation non-treated rats lose interest in the other rat and stay at a distance in a self defeating attitude (digging into litter). In treated rats interest is maintained, with enhanced proximity of animals, decrease of fear of partner and improved ability to relate as shown by signs of tenderness and attention (muzzle to muzzle approach, licking), completely absent in non treated animals.

TABLE II

|  | Number | Mean | Std. deviation | Std. Error | r |
|---|---|---|---|---|---|
| Control | 3 | 3.000 | 1.000 | 0.577 |  |
| 3 µg/kg | 3 | 5.333 | 0.577 | 0.333 | 0.0175 |
| 15 µg/kg | 3 | 4.000 | 1.000 | 0.577 | 0.2367 |
| 30 µg/kg | 3 | 4.667 | 1.155 | 0.677 | 0.0656 |

EXAMPLE 6

Behavior During Refractory Periods

Figure 10:
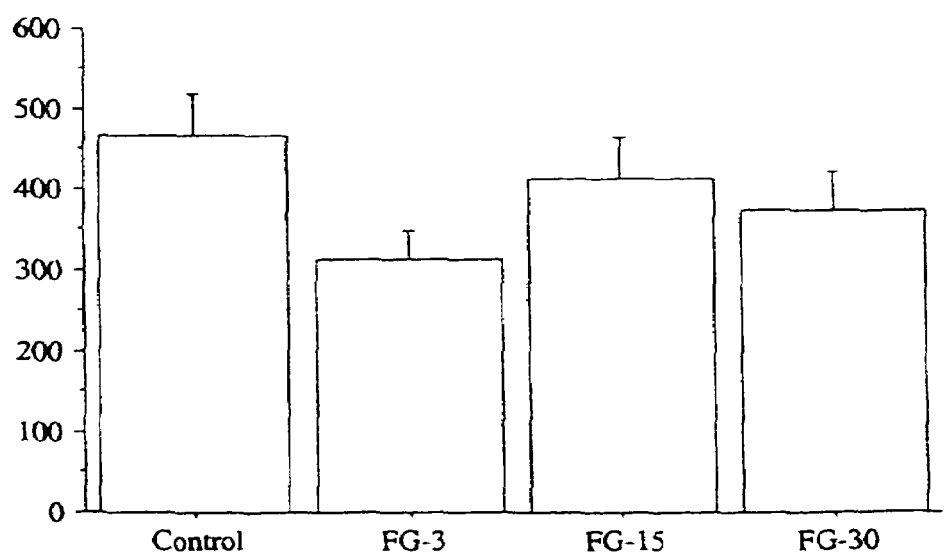
FIG. 10 shows results of a test of the refractory period between the second ejaculation and the next mount for rats administered escalating doses of a preferred embodiment of a peptide according to the invention.

There was a loss of avoidance symptoms and enhanced willingness to enter into relationship during refractory periods, the duration of which is shortened (see Table III and FIG. 10). Treated rats show a clear-cut improvement in willingness to enter into relationship with the other rat, increasingly respond to attempts of social interaction, completely loose the avoidance pattern behavior seen in control rats.

TABLE III

|  | Number | Mean (sec.) | Std. Deviation | Std. Error | r |
|---|---|---|---|---|---|
| Control | 3 | 467.333 | 87.763 | 50.670 |  |
| 3 µg/kg | 3 | 311.333 | 66.516 | 38.403 | 0.0476 |
| 15 µg/kg | 3 | 412.000 | 87.430 | 50.478 | 0.4311 |
| 30 µg/kg | 3 | 373.667 | 83.393 | 48.147 | 0.1981 |

EXAMPLE 7

Dose-Response Relationship of FG-005 Peptide on the Male Rat Sexual Behavior

Effect of increasing concentrations of FG-005 peptide (SMR1-QHNPR) given i.v. on the number of sexual intercourse episodes of male rats with sexually receptive female, was assessed. All of the qualitative parameters were analyzed using one-way analysis of variance (ANOVA) for the differences between treated groups and followed by the multiple comparison test of Fisher (PLSD Fisher) to compare each group of FG-005-injected rats with the control group (vehicle-injected rats). Nine to ten rats were used for each group and P value of less than 0.005 was considered as significant for both tests.

At the doses of 0.03 µg-1 µg and 3 µg/Kg, FG-005 peptide induced improvement on the male rat sexual behavior, during the 45-min-period of observation. This is appreciated by the significant dose-dependent increase of sexual interactions (mounts, mounts with intromission and mounts per ejaculation) during (first ejaculation latency and interejaculatory latency) episodes of sexual intercourse.

Figure 11:
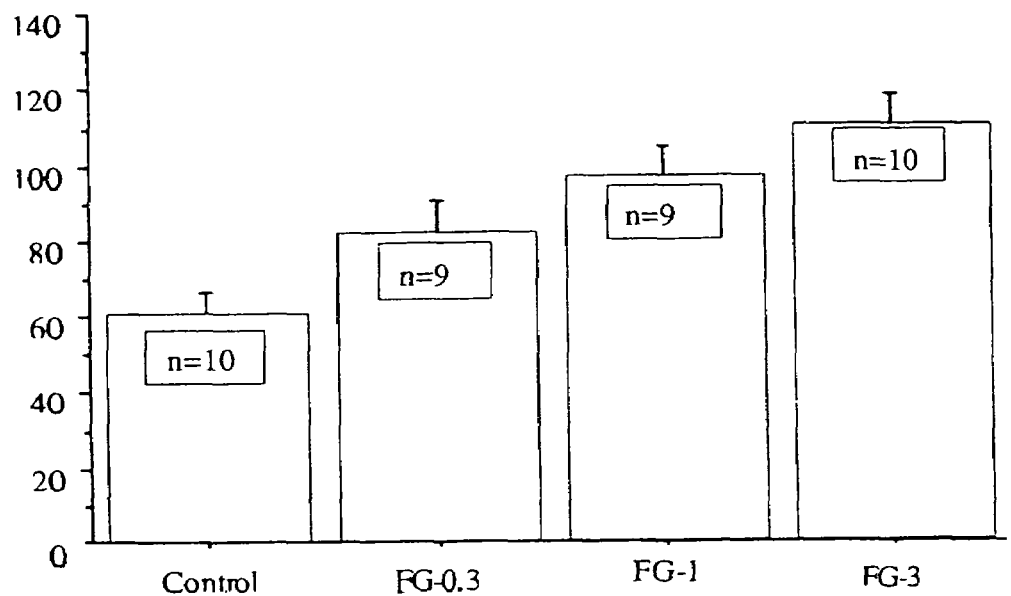
FIG. 11 is a graphic representation of the effect of increasing concentrations of FG-005 peptide (SMR1-QHNPR) on the number of mounts.
Figure 12:
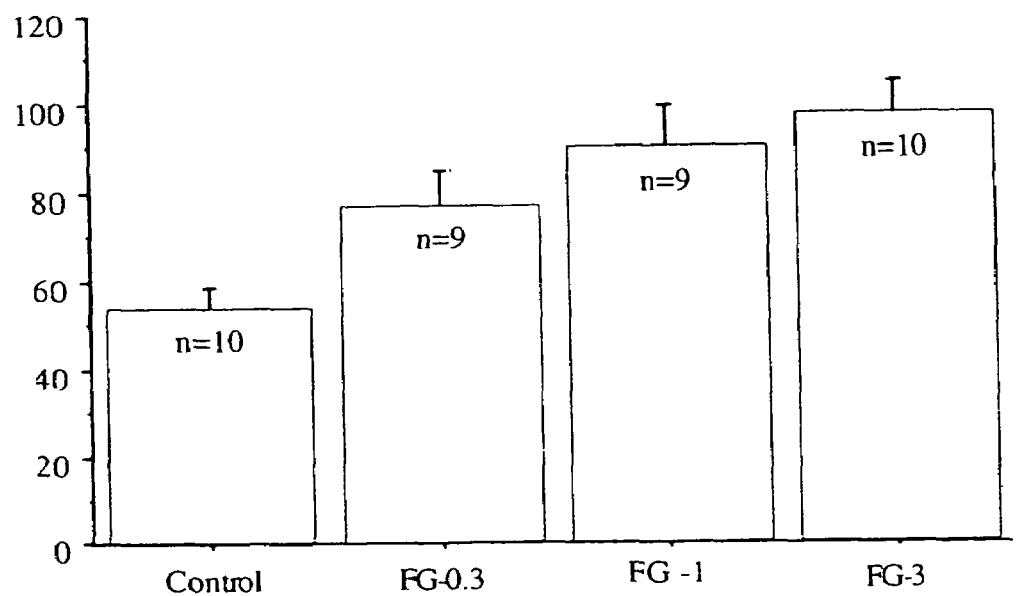
FIG. 12 is a graphic representation of the effect of increasing concentrations of FG-005 peptide (SMR1-QHNPR) on the number of mounts with intromission.
Figure 13:
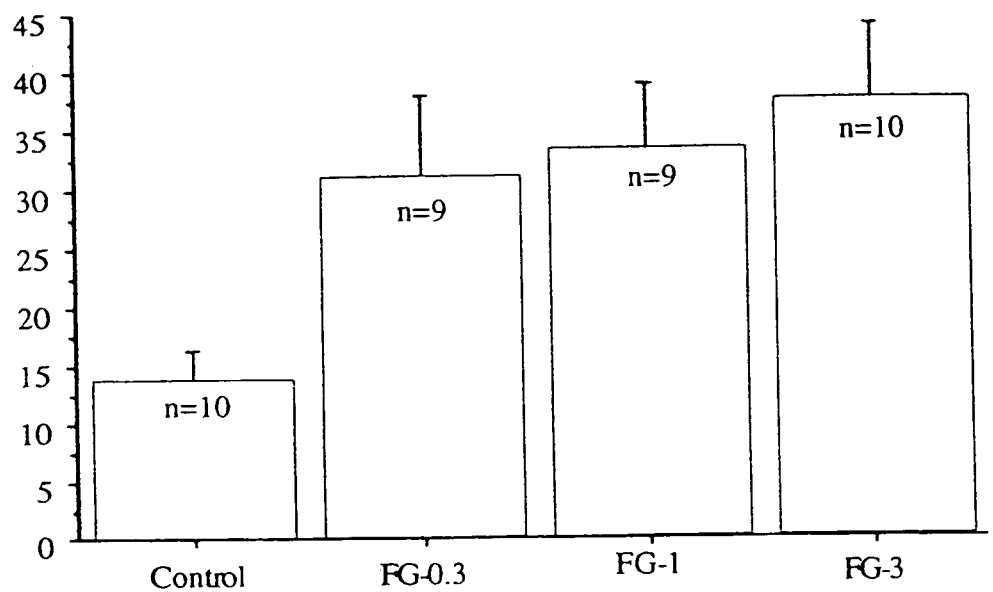
FIG. 13 is a graphic representation of the effect of increasing concentrations of FG-005 peptide (SMR1-QHNPR) on the number of mounts before the first ejaculation.
Figure 14:
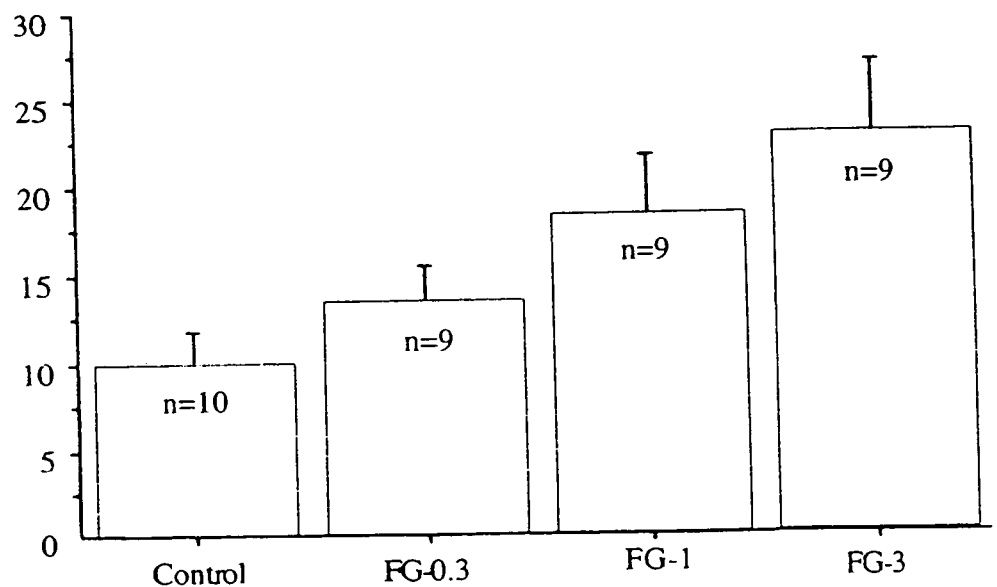
FIG. 14 is a graphic representation of the effect of increasing concentrations of FG-005 peptide (SMR1-QHNPR) on the number of mounts before the third ejaculation.
Figure 15:
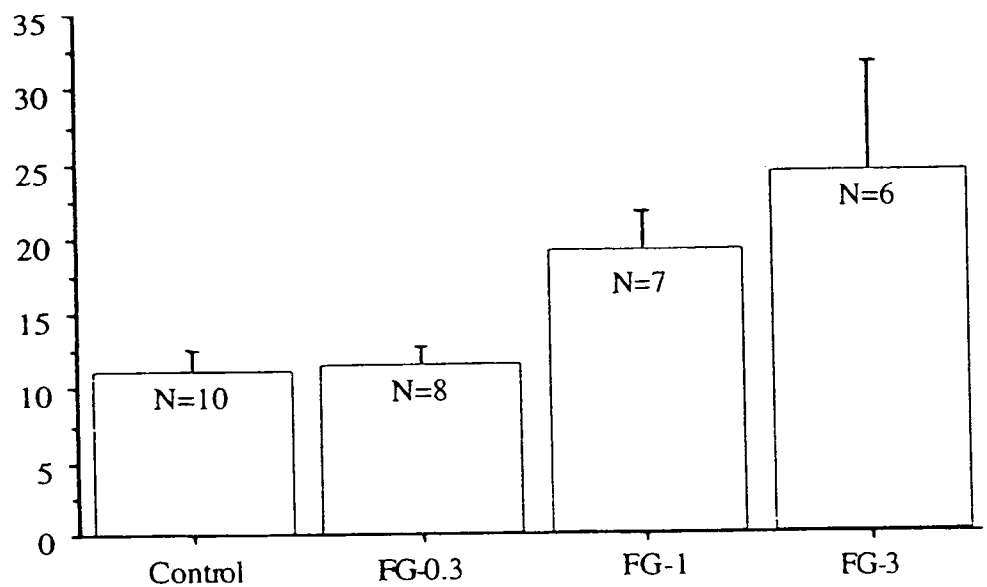
FIG. 15 is a graphic representation of the effect of increasing concentrations of FG-005 peptide (SMR1-QHNPR) on the number of mounts before the fourth ejaculation.
Figure 16:
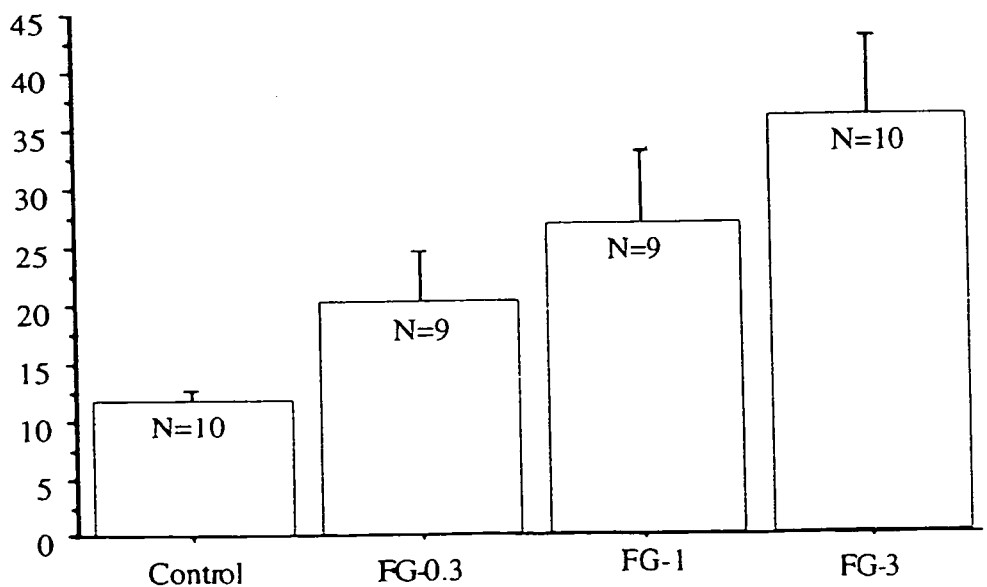
FIG. 16 is a graphic representation of the effect of increasing concentrations of FG-005 peptide (SMR1-QHNPR) peptide on the mean number of mounts per ejaculation.

FG-005-treated rats exhibit a significant increase with a dose-dependent relationship of the total number of mounts with or without intromission, p=0.0003 by ANOVA of 9-10 rats per dose (FIG. 11 and Table IV); of the number of mounts with intromission, p=0.0006 by ANOVA of 9-10 rats per dose (FIG. 12 and Table V); of the number of mounts before the first ejaculation, p=0.019 by ANOVA of 9-10 rats per dose (FIG. 13 and Table VI); of the number of mounts during interejaculatory intervals, p=0.017 by ANOVA of 9-10 rats per dose (FIG. 14 and Table VII) and p=0.025 by ANOVA of 6-10 rats per dose (FIG. 15 and Table VIII); and of the number of mount per ejaculation, p=0.011 by ANOVA of 9-10 rats per dose (FIG. 16 and Table IX).

As the number of sexual intercourse (mounts) increased before and during the ejaculatory intervals, parallely the first ejaculation latency of FG-005—treated rats increased significantly compared to vehicle—injected rats at the dose of 3 µg/Kg (p=0.03, n=10 rats versus vehicle—injected rats, n=10). And this is particularly appreciated by the significant dose-related prolongation of the second ejaculation latency, with a P value of 0.048 by ANOVA for 9-10 rats per dose and a pronounced effect at 1 and 3 µg/Kg. In the same way, the third ejaculation latency tended also to increase in a dose-related manner.

In this set of experiments, during the 45 min observation period, as the moments of social intercourse signs displayed by the male towards the female (sniffing, grooming, anogenital exploration and mount) and of attention signs to personal toilet displayed by the male, are prolongated, and the total number of ejaculations of FG-005-treated rats tended to be diminished, and was lower than that of vehicle-treated rats at the dose of 3 µg/Kg (p=0.04, n=10 rats per group).

In general, there was in FG-005-treated rats a loss of aggressive impulse behavior seen in control rats.

TABLE IV

|  | Number | Mean | Deviation | Error |
|---|---|---|---|---|
| Control | 10 | 61.100 | 15.892 | 5.025 |
| FG-0.3 | 9 | 81.778 | 26.729 | 8.910 |
| FG-1 | 9 | 96.667 | 24.027 | 8.910 |
| FG-3 | 10 | 110.100 | 25.265 | 7.990 |

TABLE V

|  | Number | Mean | Deviation | Error |
|---|---|---|---|---|
| Control | 10 | 54.100 | 14.955 | 4.729 |
| FG-0.3 | 9 | 77.111 | 23.945 | 7.982 |
| FG-1 | 9 | 90.556 | 26.735 | 8.912 |
| FG-3 | 10 | 97.700 | 22.226 | 7.029 |

TABLE VI

|         | Number | Mean   | Deviation | Error |
|---------|--------|--------|-----------|-------|
| Control | 10     | 13.800 | 8.080     | 2.555 |
| FG-0.3  | 9      | 31.111 | 20.368    | 6.789 |
| FG-1    | 9      | 33.444 | 16.356    | 5.452 |
| FG-3    | 10     | 37.500 | 20.195    | 6.386 |

TABLE VII

|         | Number | Mean   | Deviation | Error |
|---------|--------|--------|-----------|-------|
| Control | 10     | 10.000 | 5.578     | 1.764 |
| FG-0.3  | 9      | 13.444 | 5.918     | 1.973 |
| FG-1    | 9      | 18.333 | 9.849     | 3.283 |
| FG-3    | 9      | 22.889 | 12.057    | 4.019 |

TABLE VIII

|         | Number | Mean   | Deviation | Error |
|---------|--------|--------|-----------|-------|
| Control | 10     | 11.100 | 4.483     | 1.418 |
| FG-0.3  | 8      | 11.500 | 3.338     | 1.180 |
| FG-1    | 7      | 19.143 | 6.256     | 2.365 |
| FG-3    | 6      | 24.167 | 18.060    | 7.373 |

TABLE IX

|         | Number | Mean   | Deviation | Error |
|---------|--------|--------|-----------|-------|
| Control | 10     | 11.733 | 3.413     | 1.079 |
| FG-0.3  | 9      | 20.220 | 12.976    | 4.325 |
| FG-1    | 9      | 26.911 | 18.092    | 6.031 |
| FG-3    | 10     | 36.013 | 21.462    | 6.787 |

EXAMPLE 8

Effect of FG-005 Peptide (SMR1-QHNPR) on the First Two Post Ejaculatory Intervals (PEI)

a) Effect of FG-005 Peptide on the Duration of PEI

All quantitative results are statistically analyzed using a Krukal-Wallis test (KWT), as a between-group variable, followed by Mann-Whitney U-test (MWT) to compare the treated group to control one. Friedman test (FT), as within-group variable, was used for repeated measures across the first three ejaculatory series, followed by Wilcoxon (WT). Data are reported as mean ±SEM. For all statistical evaluations, the level of significance was set at $p<0.05$. All statistical analyses were carried out using the Statview™ 4.5 statistical package (Abacus Concepts, Inc, Berkeley, Calif.).

Figure 17:
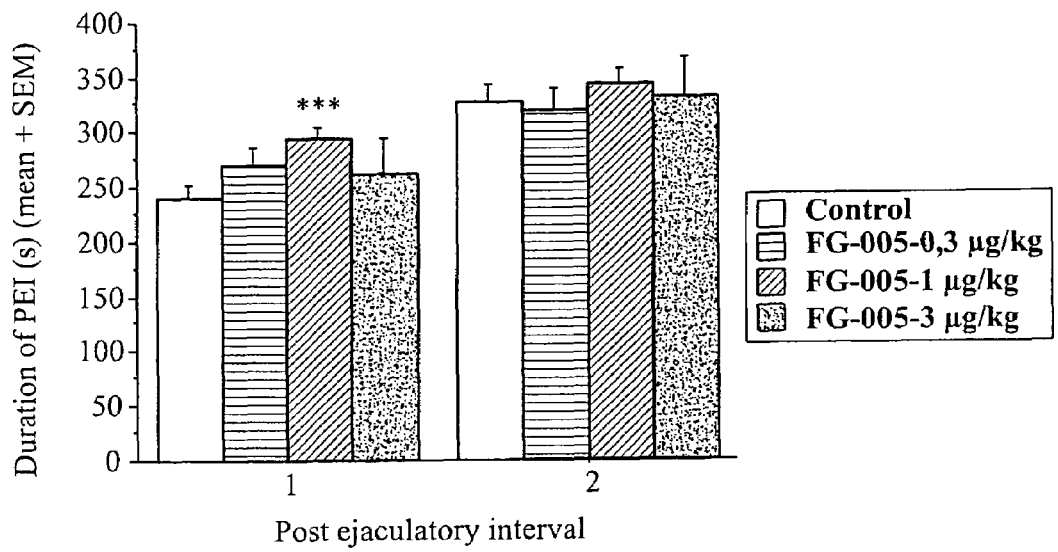
FIG. 17 is a graphic representation of the effect of FG-005 peptide (SMR1-QHNPR) on the duration of the first two post ejaculatory intervals (PEI).

The KWT showed an approached significant heterogeneity among the duration of the first post ejaculatory interval of the four groups (Hdf3=7.17, $p=0.067$). Although the KWT test did not reach a significant level, further analysis was conducted. As shown in FIG. 17, the first PEI was found to be significantly longer in FG-005-treated rats at the dose of 1 μg/kg than in control ones (MWT: U=8, $p=0.005$). PEI of rats treated with FG-005 at the doses of 0.3 and 31 g/kg did not differ from that of control rats (MWT: U=24, $p=0.16$ and U=39, $p=0.93$, respectively).

The second PEI was not significantly influenced following FG-005 treatment (KWT: Hdf3=1.08, $p=0.78$).

There was no significant dose-response relationship in the FG-005 effect on PEI duration. Indeed, FG-005 treatment prolonged the PEI duration across ejaculations compared to control group, only at 1 μg/kg dose and for the first PEI. Furthermore, the 3 μg/kg-dose, which exerted predominant enhancing effect on the frequency of intromissions within each three successive ejaculatory sequence, had no effect on the duration of the first as well as the second PEI.

b) Effect of FG-005 on the Duration of Male Immobility During PEI

Figure 18A:
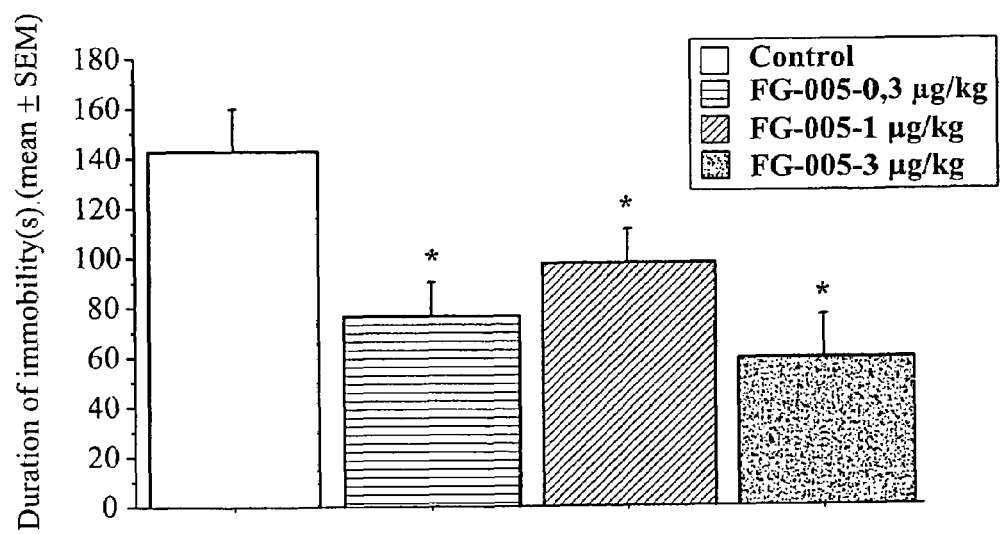
FIG. 18 is a graphic representation of the effect of FG-005 peptide (SMR1-QHNPR) on the duration of male immobility during the first two PEI (18A and 18B).
Figure 18B:
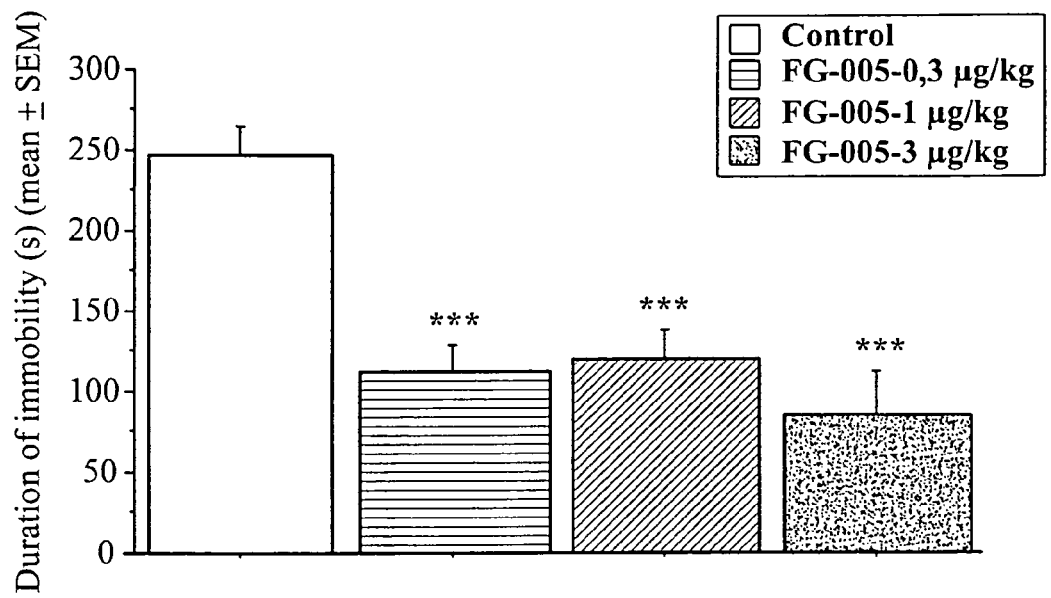

Among the four treatment groups, KWT showed an overall heterogeneity on the duration of male immobility during the first and the second PEI (Hdf3=11.68, $p<0.009$ and Hdf3=18.21, $p<0.001$, respectively). As shown in FIG. 18, FG-005-treated males, at 0.3, 1 and 3 μg/kg doses, spent significantly less time away from the female and totally immobile compared to vehicle controls during the two successive post-ejaculatory intervals; FG-005-0.3 μg/kg, MWT: U=13, $p=0.016$ and U=0, $p=0.0004$, respectively; FG-005-1 μg/kg: MWT: U=13, $p=0.016$ and U=5, $p=0.0019$, respectively; FG-005-3 μg/kg: MWT: U=12, $p=0.013$ and U=7, $p=0.0034$, respectively.

c) Effect of FG-005 on the Duration of Male Socio-Sexual Behaviors During PEI

Figure 19A:
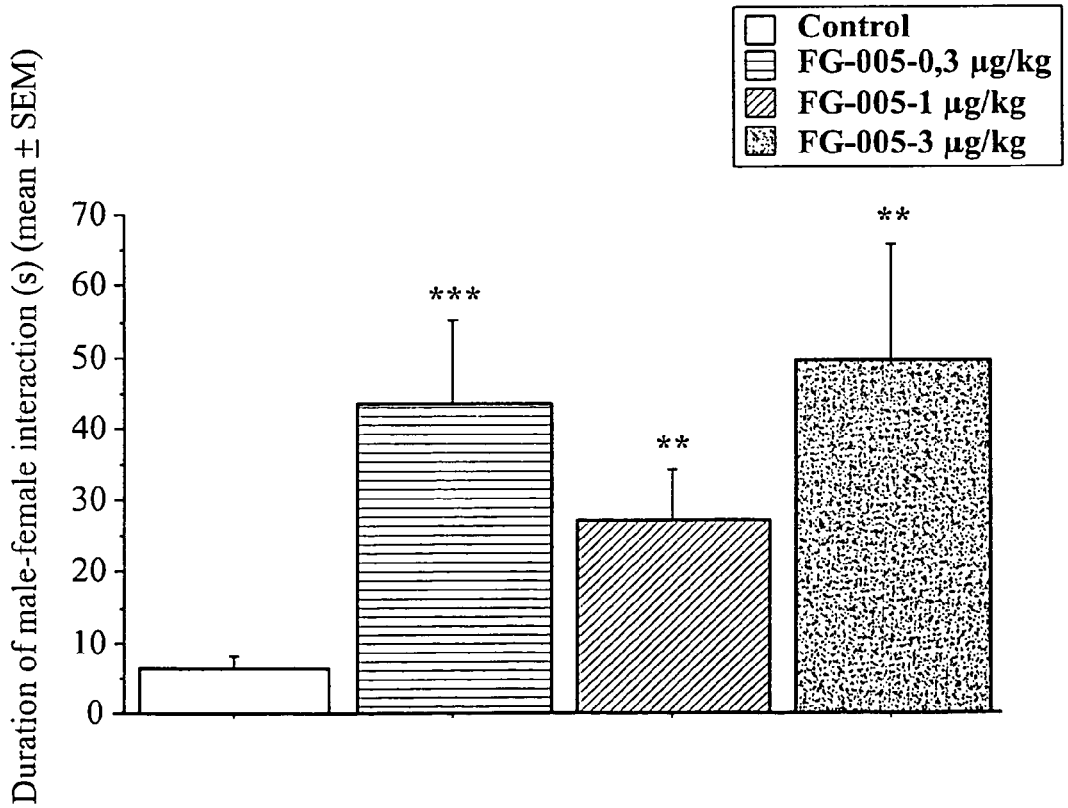
FIG. 19 is a graphic representation of the effect of FG-005 peptide (SMR1-QHNPR) on the duration of male sociosexual behaviors during the first two PEI (19A and 19B).
Figure 19B:
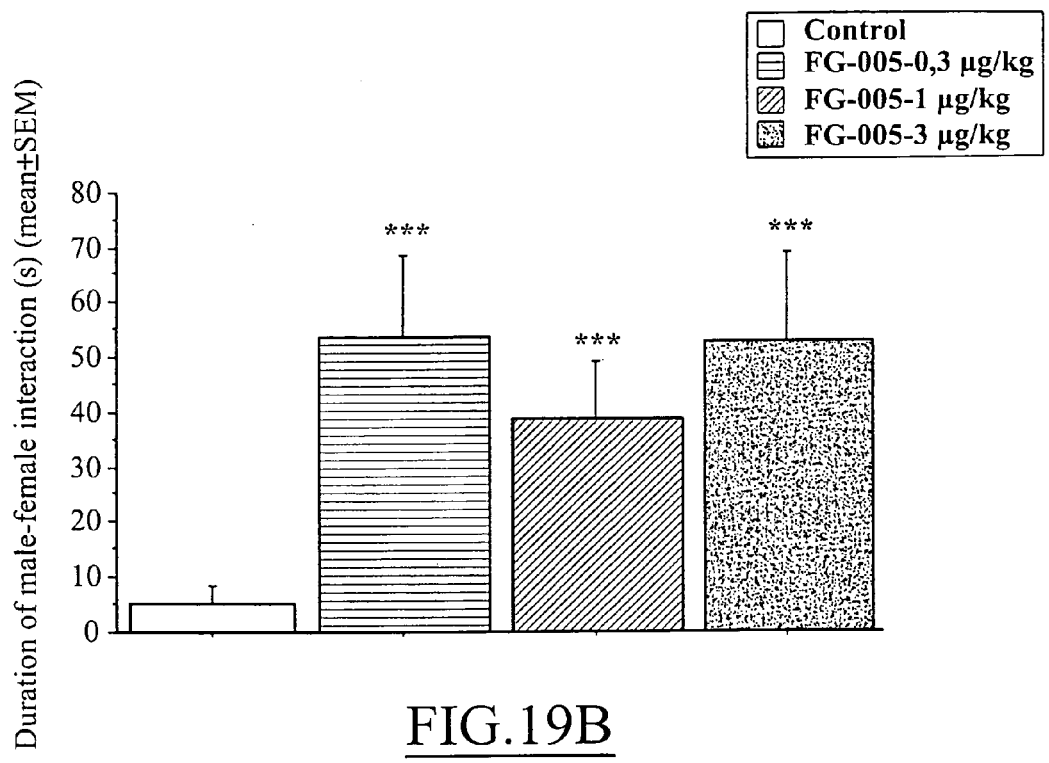

Among the four treatment groups, KWT showed an overall heterogeneity on the duration of socio-sexual interactions during the first and the second PEI (Hdf3=13.30, $p<0.005$, and Hdf3=15.66, $p<0.002$, respectively). As shown in FIG. 19, FG-005-treated males, at the doses of 0.3, 1 and 3 μg/kg, spent significantly more time orienting towards and pursuing the female and ano-genital sniffing and grooming, compared to controls during the two successive post-ejaculatory intervals; FG-005 0.3 μg/kg, MWT: U=4.5, $p=0.0015$ and U=5, $p=0.0017$, respectively; FG-005-1 μg/kg: MWT: U=11, $p=0.0096$, and U=6, $p=0.002$, respectively; FG-005-3 μg/kg: MWT: U=10.5, $p=0.0084$ and U=5, $p=0.0018$, respectively Masculine sociosexual behaviors other than copulatory acts were measured and analyzed during the two successive post-ejaculatory intervals. Among these are pursuit of the female, sniffing, grooming, running behind the partner in close contact and anogenital exploration (sniffing, licking and grooming the partner). Compared to vehicle controls, the propensity of FG-005-treated males, based on the amount of time spent orienting towards and pursuing the female, was highly increased whilst that of time spent alone totally immobility followed the inverse pattern. Thus, for a similar amount of time in PEI duration compared to controls, the 3 μg/kg-treated rats spent during this interval, 7 to 10 fold more amount of time to pursue and groom the female.

EXAMPLE 9

Anti-Depressive Effect of FG-005 in the Behavioral Despair Test

Forty male Wistar/AF EOPS rats (Iffa-Credo Breeding Centre, 69-St-Germain sur l'Arbresle, France), weighing 300 to 320 g, were used. On arrival, the rats were labelled and distributed randomly in pairs into type F polycarbonate cages (48×27×20 cm, U.A.R., 91-Epinay-Sur-Orge, France). The animals were stabled in an air-conditioned animal house, at a temperature of 22-24° C. The rats were given food (M25 croquettes, Ets Piétrement, 77-Provins, France) and drink ad libitum and were subjected to a 12-hour light-darkness cycle.

After one week of familiarization with the laboratory conditions, the rats were weighed and distributed randomly into 3 treatment groups (n=12). The rats of the different groups will all be handled in the same way and under the same conditions.

The behavioral despair test takes place over two sessions:
a 15-minute test session;
a 5-minute retest session, performed 24 hours later.

During the test session, the rat was subjected to forced swimming in a Plexiglas cylinder (20 cm in diameter and 50 cm in height, containing 25 cm of water at 25° C.) and its behavior was recorded over 15 minutes. At the end of the test, the rat was removed from the water, dried gently, treated and then returned to its dwelling cage.

During the retest, 24 hours later, the rat was again placed in the water and its behavior was recorded over 5 minutes.

The recorded variables are the period of immobility during the first 5 minutes of both the test and the retest.

The peptide FG-005 was suspended at a rate of 500 µg per 5 ml of 0.01N acetic acid, and then diluted with PBS to be administered at doses of 50 and 100 µg/kg via the i.v. route into the dorsal caudal vein of the rat, immediately after the test and 300 and 5 minutes before the retest the following day (Table X). 8-OH-DPAT was injected i.p.

TABLE X

| Group | Rat per group | Treatment | Dose (µg/kg) | Volume (ml/kg) | Administrations before the retest (minutes) |
|---|---|---|---|---|---|
| Vehicle | 10 | Acetic acid + PBS | — | 0.7 | 1440, 300, 5 |
| FG 50 | 10 | FG-005 | 50 | 0.7 | 1440, 300, 5 |
| FG 100 | 10 | FG-005 | 100 | 0.7 | 1440, 300, 5 |
| 8-OH-DPAT | 10 | 8-OH-DPAT | 500 | 1 | 1440, 300, 30 |

Figure 20:
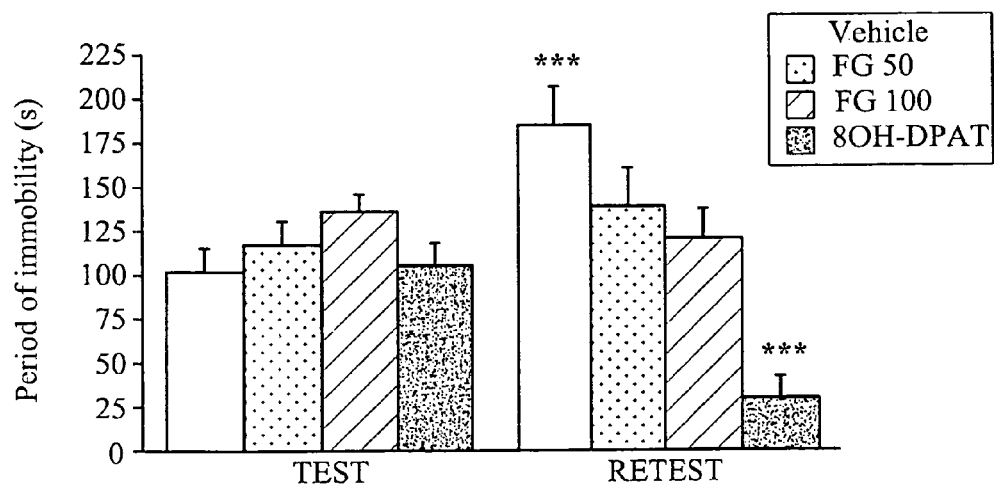
FIG. 20 is a graphic representation of the effect of increasing concentration of FG-005 peptide (SMR1-QHNPR) on the periods of immobility during the test and the retest in the Behavioral Despair test.

ANOVA in factorial measurements was used to demonstrate the existence of heterogeneity among the groups. A bilateral probability paired t test was used to compare the two periods of immobility of the test with those of the retest in each of the groups. The results are expressed as an average standard error of mean (SEM) (Table XI and FIG. 20). The statistical and graphical processing was performed using Statview5 and DeltaGraph® Pro 3.5 software.

The analysis of variance [$F(3.36)=1.57$; N.S.] shows no heterogeneity of the periods of immobility for the different groups during the test 1 before any treatment and reveals a heterogeneity among these periods of immobility after treatment [$F(3.36)=13.12$; $p<0.001$].

The bilateral probability paired t test shows that the control rats significantly increase their period of immobility during the retest compared with the test. Conversely, the rats treated with 8-OH-DPAT significantly reduce their period of immobility during the retest compared with the test.

The immobility time of the rats treated with FG-005 at a dose of 50 µg/kg increase their period of immobility during the retest and those treated at a dose of 100 mg/kg reduce it. However, in both cases, the differences are not statistically significant.

TABLE XI

Immobility periods during the test and retest sessions (mean ± SD)

| | Vehicle i.v. (n = 10) | FG-50 50 µg/kg, i.v. (n = 10) | FG-100 100 µg/kg, i.v. (n = 10) | 8-OH-DPAT 0.5 mg/kg, i.p. (n = 10) |
|---|---|---|---|---|
| Test | 104.80 ± 11.08 | 119.00 ± 13.79 | 138.30 ± 11.03 | 109.20 ± 11.43 |
| Retest | 187.80 ± 20.41 | 141.20 ± 21.28 | 121.50 ± 17.47 | 31.60 ± 11.51 |
| Paired t test (bilat. prob.) (Test vs. Retest) | t = 4.14; p < 0.005 | t = 1.50; N.S. | t = 1.20; N.S. | t = 10.91; p < 0.001 |

NS: Not Significant

Under our experimental conditions, the period of immobility of the control rats is significantly longer during the retest compared with the test. This clearly shows the resignation of the rats, which no longer seek to escape the rainy aquatic environment.

The rats treated with the peptide FG-005, at doses of 50 and 100 µg/kg, i.v., immediately after the depression test and 300 and 5 minutes before the retest the following day, do not increase their periods of immobility during the retest. The rats of the two groups show equivalent swimming activity during the two sessions. Since the rats showed no behavioral resignation, the peptide FG-005 is thought to have an antidepressant effect in rats. 8-OH-DPAT, used as reference substance, showed significant anti-resignation effect.

What is claimed is:

1. A method for increasing sexual arousal comprising: parenterally administering to a male mammal in need thereof an effective amount of a composition containing an SMR1 peptide comprising SEQ ID NO: 2 that is sufficient to increase sexual arousal in said male mammal.

2. The method of claim 1, wherein said male mammal exhibits a sexual arousal disorder.

3. The method of claim 1, wherein said male mammal exhibits is impaired sexual behavior.

4. The method of claim 1, wherein the male mammal exhibits hypoactive sexual desire disorder.

5. The method of claim 1, wherein the route of administration is intravenous.

6. A method for increasing sexual arousal comprising: parenterally administering an effective amount of a peptide comprising SEQ ID NO: 2 to a male mammal in need thereof.

7. The method of claim 6, wherein said mammal has impaired sexual behavior.

8. The method of claim 6, wherein said mammal has hypoactive sexual desire.

9. The method of claim 6, wherein said mammal has untimely ejaculation.

10. The method of claim 6, wherein said peptide consists of SEQ ID NO: 2.

11. The method of claim 6, wherein said peptide is administered parenterally.

12. The method of claim 6, wherein said peptide is administered intravenously.

13. The method of claim 6, wherein said mammal is human.

14. A method for inducing or increasing sexual arousal in a male mammal comprising: parenterally administering to said male mammal an amount of an SMR 1 peptide that comprises SEQ ID NO: 2 effective to increase sexual arousal in said mammal compared to a similar male mammal to which said SMR1 peptide has not been administered.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: This is a peptide sequence that was designed
      to achieve therapeutic effects in mammals.
<220> FEATURE:
<221> NAME/KEY: MISC_FEATURE
<222> LOCATION: (1)..(1)
<223> OTHER INFORMATION: Xaa is Glp

<400> SEQUENCE: 1

Xaa His Asn Pro Arg
 1               5

<210> SEQ ID NO 2
<211> LENGTH: 5
<212> TYPE: PRT
<213> ORGANISM: Artificial Sequence
<220> FEATURE:
```

```
<223> OTHER INFORMATION: This is a peptide sequence that was designed
      to achieve therapeutic effects in mammals.

<400> SEQUENCE: 2

Gln His Asn Pro Arg
 1               5

<210> SEQ ID NO 3
<211> LENGTH: 4
<212> TYPE: PRT
<213> ORGANISM: Artificial Sequence
<220> FEATURE:
<223> OTHER INFORMATION: This is a peptide sequence that was designed to
      achieve therapeutic effects in mammals.
<220> FEATURE:
<221> NAME/KEY: MISC_FEATURE
<222> LOCATION: (1)..(1)
<223> OTHER INFORMATION: Xaa is Glp

<400> SEQUENCE: 3

Xaa His Asn Pro
 1

<210> SEQ ID NO 4
<211> LENGTH: 4
<212> TYPE: PRT
<213> ORGANISM: Artificial Sequence
<220> FEATURE:
<223> OTHER INFORMATION: This is a peptide sequence that was designed to
      achieve therapeutic effects in mammals.

<400> SEQUENCE: 4

Gln His Asn Pro
 1

<210> SEQ ID NO 5
<211> LENGTH: 6
<212> TYPE: PRT
<213> ORGANISM: Artificial Sequence
<220> FEATURE:
<223> OTHER INFORMATION: This is a peptide sequence that was designed to
      achieve therapeutic effects in mammals.

<400> SEQUENCE: 5

Arg Gln His Asn Pro Arg
 1               5

<210> SEQ ID NO 6
<211> LENGTH: 11
<212> TYPE: PRT
<213> ORGANISM: Artificial Sequence
<220> FEATURE:
<223> OTHER INFORMATION: This is a peptide sequence that was designed to
      achieve therapeutic effects in mammals.

<400> SEQUENCE: 6

Val Arg Gly Pro Arg Arg Gln His Asn Pro Arg
 1               5                  10

<210> SEQ ID NO 7
<211> LENGTH: 5
<212> TYPE: PRT
<213> ORGANISM: Artificial Sequence
<220> FEATURE:
<223> OTHER INFORMATION: This is a peptide sequence that was designed to
      achieve therapeutic effects in mammals.

<400> SEQUENCE: 7
```

```
Gln His Asn Leu Arg
  1               5

<210> SEQ ID NO 8
<211> LENGTH: 6
<212> TYPE: PRT
<213> ORGANISM: Artificial Sequence
<220> FEATURE:
<223> OTHER INFORMATION: This is a peptide sequence that was designed to
      achieve therapeutic effects in mammals.

<400> SEQUENCE: 8

Arg Gln His Asn Leu Arg
  1               5

<210> SEQ ID NO 9
<211> LENGTH: 6
<212> TYPE: PRT
<213> ORGANISM: Artificial Sequence
<220> FEATURE:
<223> OTHER INFORMATION: This is a peptide sequence that was designed to
      achieve therapeutic effects in mammals.

<400> SEQUENCE: 9

Gly Gln His Gly Pro Arg
  1               5

<210> SEQ ID NO 10
<211> LENGTH: 6
<212> TYPE: PRT
<213> ORGANISM: Artificial Sequence
<220> FEATURE:
<223> OTHER INFORMATION: This is a peptide sequence that was designed to
      achieve therapeutic effects in mammals.

<400> SEQUENCE: 10

Gly Gln His Asp Pro Thr
  1               5
```